United States Patent [19]

Lindsay et al.

[11] Patent Number: 4,701,160
[45] Date of Patent: Oct. 20, 1987

[54] CATHETER AND METHOD FOR INFUSING FLUID INTO A PATIENT

[75] Inventors: Erin J. Lindsay, Manchester, Mich.; John N. Pittman, Carmel, Ind.

[73] Assignee: Minnesota Mining and Manufacturing Company, St. Paul, Minn.

[21] Appl. No.: 872,936

[22] Filed: Jun. 11, 1986

[51] Int. Cl.$^4$ ............................................. A61M 31/00
[52] U.S. Cl. .................................... 604/53; 604/158; 604/264
[58] Field of Search ................ 604/53, 239, 240, 250, 604/264, 96, 158, 284; 128/344, 348.1

[56] References Cited

U.S. PATENT DOCUMENTS

| | | | |
|---|---|---|---|
| 2,587,188 | 2/1952 | McFadden | 138/45 |
| 2,590,215 | 3/1952 | Sausa | 138/45 |
| 2,735,642 | 2/1956 | Norman | 251/5 |
| 2,756,959 | 7/1956 | Hill | 251/5 |
| 2,795,390 | 6/1957 | Laurenty | 251/5 |
| 2,982,511 | 5/1961 | Connor | 251/5 |
| 3,463,179 | 8/1969 | Hrdina | 137/154 |
| 3,538,917 | 11/1970 | Selker | 128/326 |
| 3,982,723 | 9/1976 | Ford et al. | 251/5 |
| 4,072,146 | 2/1978 | Howes | 604/158 |
| 4,186,740 | 2/1980 | Guerra | 604/250 |
| 4,195,637 | 4/1980 | Grüntzig et al. | 604/53 |
| 4,206,929 | 6/1980 | Bruce | 277/34 |
| 4,256,130 | 3/1981 | Smith et al. | 137/1 |
| 4,332,254 | 6/1982 | Lundquist | 128/344 |
| 4,473,067 | 9/1984 | Schiff | 604/158 |
| 4,476,877 | 10/1984 | Barker | 604/53 |
| 4,540,411 | 9/1985 | Bodicky | 604/250 |

OTHER PUBLICATIONS

"Use of Fogarty Catheter Tamponade for Ruptured Abdominal Aortic Aneurysms", *Am J Roentgenol*, 128:31-33, Jan. 1977, Anastacio C. Ng and Edward C. Ochsner.

"Emergency Control of Ruptured Abdominal Aortic Aneurysm by Transaxiallary Balloon Catheter", *Vascular Surgery*, vol. 6, pp. 79-84, 1972, Frederick Goethe Smith, M.D., F.A.C.A.

"Intra-Arterial Occlusion in Vascular Surgery", *Annals of Surgery*, vol. 171, No. 5, pp. 695-703, J. J. McCaughan, Jr., M.D., J. M. Young, M.D.

*Primary Examiner*—C. Fred Rosenbaum
*Assistant Examiner*—Gene B. Kartchner
*Attorney, Agent, or Firm*—Donald M. Sell; James A. Smith; Robert W. Hoke, II

[57] ABSTRACT

A medical catheter and a method for infusing blood into a patient. The medical catheter has first and second inlet openings, an outlet opening, a passageway connecting the openings, and a flexible valve member between the inlet openings. The valve member controls the size of the passageway between the inlet openings. The method includes inserting a conventional occlusion catheter into the medical catheter through the valve member and extending the tip of the occlusion catheter beyond the outlet opening of the medical catheter so that the blood vessel within the patient can be restrained.

4 Claims, 8 Drawing Figures

CATHETER AND METHOD FOR INFUSING FLUID INTO A PATIENT

FIELD OF THE INVENTION

This invention relates to the field of medical catheters and more particularly to catheters suitable for infusing a fluid into a patient. A method of infusing blood into a patient is also included within the scope of the invention.

BACKGROUND ART

Excessive bleeding from a blood vessel is typically treated by first opening the body and then repairing or replacing the damaged blood vessel. In the case of a ruptured aortic aneurysm or a severed descending aorta resulting from a car accident or the like, this treatment may be life threatening due, in part, to loss of blood pressure when the body is opened. This loss of blood pressure may stop the heart and risk ischemic damage to the brain and other vital organs.

Present techniques for the repair or replacement of a damaged aorta generally involve opening the abdomen of the patient, locating the damage and effectuating the repair or replacement. Upon opening the abdomen, an instant decompression may occur, and coronary blood pressure may be lost. This may stop the heart from beating and may lead to the ischemic damage referred to earlier. When the heart stops, a surgical staff member typically manually massages the heart. At the same time, the blood is suctioned from the patient's abdomen, processed and returned to the patient along with additional blood from a blood bank to restore the correct volume of blood.

Also, at the same time, the damaged portion of the aorta must be located and repaired or replaced. Many times the damaged portion lies beneath the intestines which must be moved. But this can be difficult to determine until the blood is suctioned off.

SUMMARY OF THE INVENTION

The present invention provides a medical catheter suitable for infusing fluid into a patient which, when used according to the method of the present invention, can minimize the loss of blood pressure and the attendant problems previously described. According to the invention, there is provided a medical catheter suitable for use with a conventional occlusion catheter for rapidly infusing fluid into a patient. The conventional occlusion catheter has an inlet opening, an expandable occluder and a through passageway between the inlet opening and the expandable occluder. The medical catheter of the present invention has a first inlet opening, a second inlet opening spaced a distance from the first inlet opening, an outlet opening, a passageway connecting the openings, and valve means between the first and second inlet openings. The first inlet opening, the outlet opening and the through passageway are dimensioned to receive the occlusion catheter. The valve means can control the size of a portion of the passageway between the inlet openings. This portion of the passageway can be closed to restrain the passage of fluid through the first inlet opening, and this portion of the passageway can be closed around the occlusion catheter, when the occlusion catheter is received within the medical catheter, to restrain the passage of fluid through the first inlet opening.

The valve means is preferably a valve member comprising an outer tube, an inner, flexible tube, two support bands spaced apart within the inner tube, means for sealing the outer tube to the inner tube opposite the support bands, and a portion of the outer tube having an aperture therethrough between the support bands, so that a fluid can be passed through the aperture to distend the inner, flexible tube and thereby control the size of the passageway through the inner tube between the support bands.

Also, according to the invention, there is provided a method of infusing blood into a patient to increase the blood pressure of the patient upstream of an aortic rupture using the previously described medical and occlusion catheters. The method includes inserting the medical catheter into a patient's aorta, infusing blood through the medical catheter to raise the blood pressure, inserting the occlusion catheter into the medical catheter, extending the occluder of the occlusion catheter into the aorta, and expanding the occluder to restrain the flow of the fluid within the aorta from passing the occluder, whereby the portion of the cardiovascular system upstream of the aortic rupture is isolated from the portion of the cardiovascular system downstream of the aortic rupture, so that the patient's abdomen can be opened with decreased risk of loss of coronary blood pressure. Preferably, this method further includes infusing additional blood through the medical catheter to further raise the blood pressure upstream of the aortic rupture.

BRIEF DESCRIPTION OF THE DRAWING

Other advantages of the invention will become apparent from the following drawing wherein like numerals refer to like parts.

DETAILED DESCRIPTION

Figure 1:
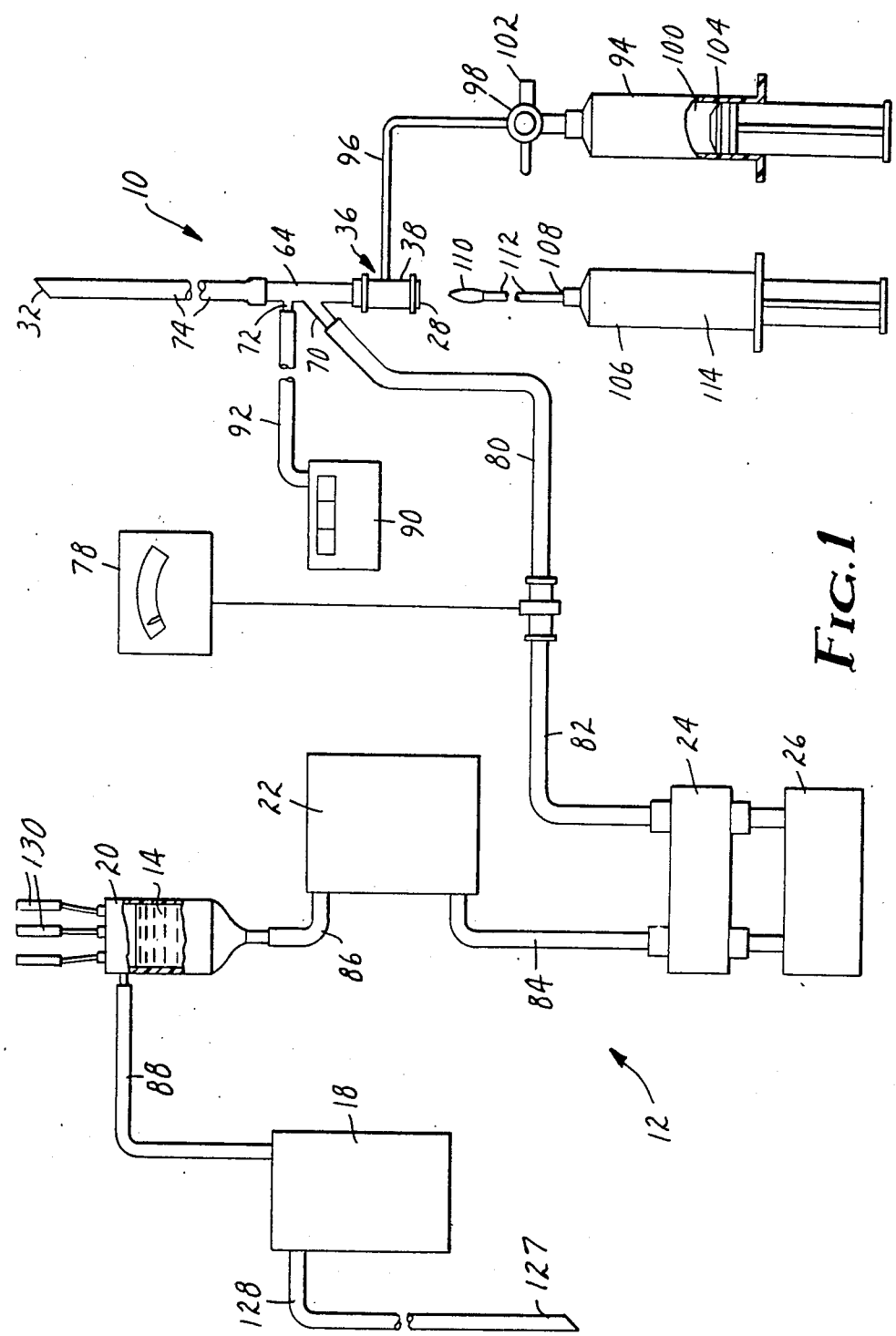
FIG. 1 is a schematic view of a preferred embodiment of the medical catheter of the present invention, including a preferred valve member, in a system suitable for rapidly infusing blood into a patient.
Figure 8:
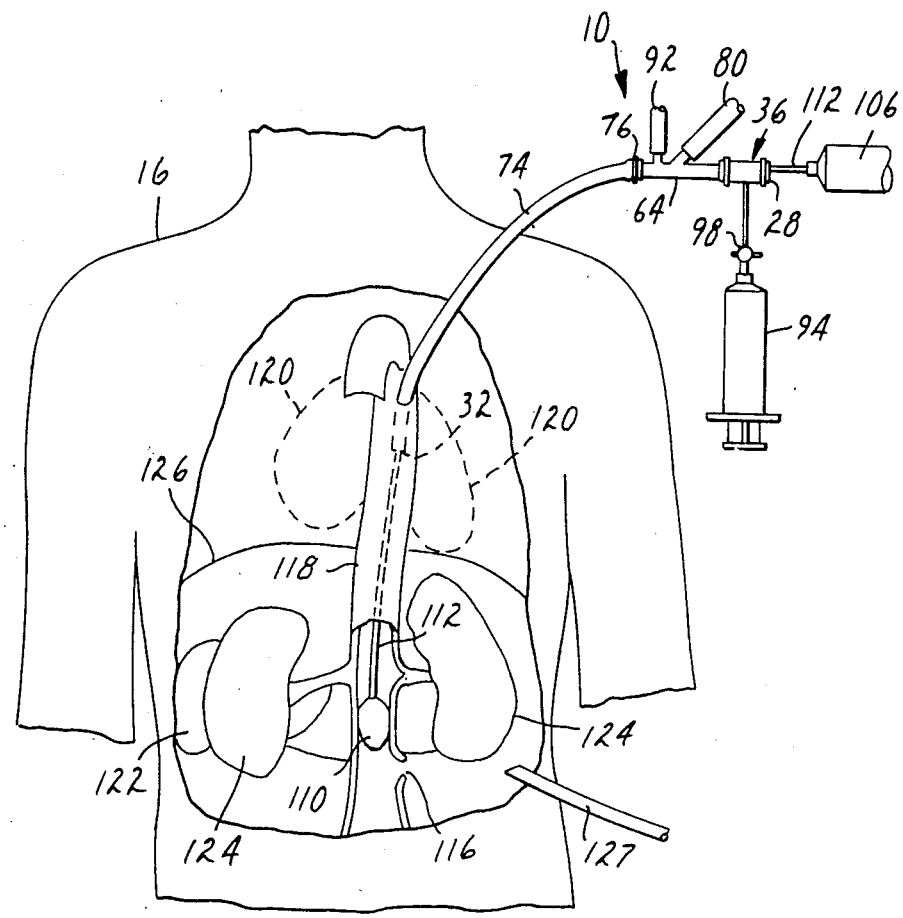
FIG. 8 is a schematic view of the medical catheter of FIG. 1 inserted into a descending aorta of a patient with portions broken away to illustrate an occlusion catheter received within the medical catheter and extending beyond the medical catheter to a place upstream of a ruptured aortic aneurysm.

Referring to the figures of the drawing, there is shown in FIG. 1 a schematic view a preferred embodiment of the medical catheter 10 of the present invention in a system 12 suitable for rapidly infusing blood 14 into a patient 16, as shown in FIG. 8. The system 12 is generally comprised of a blood separator 18, a blood reservoir 20, a blood pump 22, a heat exchanger 24, a heater 26 and the medical catheter 10. In operation, the blood 14 is pumped by the pump 22 from the reservoir 20, through the heat exchanger 24, and to the medical catheter 10, from which the blood 14 can be infused into the patient 16 by a method to be described.

Figure 2:
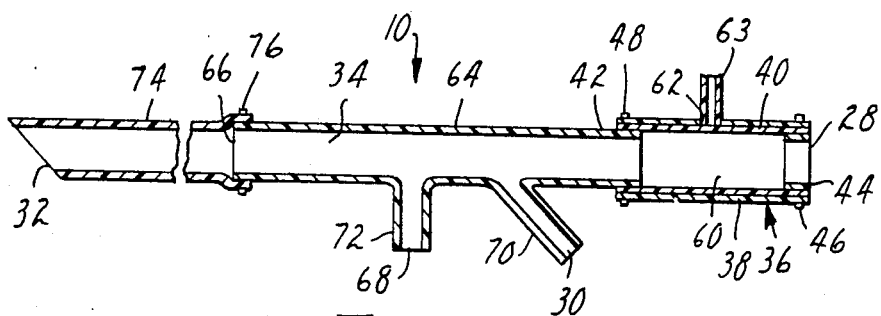
FIG. 2 is a longitudinal, cross-sectional view of the medical catheter of FIG. 1.

The medical catheter 10 is shown in longitudinal cross-sectional view in FIG. 2 to comprise a tubular member having a first inlet opening 28, a second inlet opening 30 in the wall of the tubular member that is spaced a distance from the first inlet opening 28, an outlet opening 32, a through passageway 34 connecting the openings 28, 30 and 32, and a flexible valve member 36 between the first and second inlet openings 28 and 30.

Figure 4:
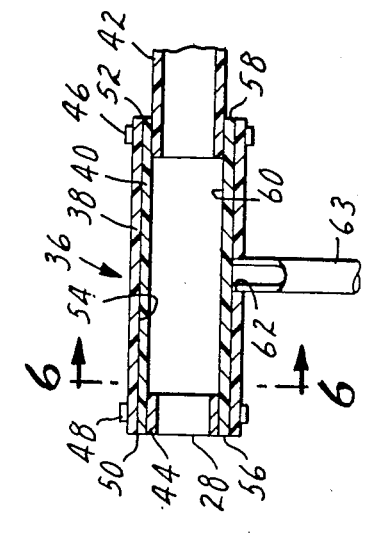
FIG. 4 is a longitudinal, cross-sectional view of the valve member of FIG. 1 in the open position.
Figure 3:
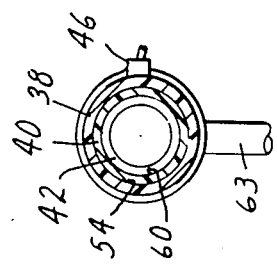
FIG. 3 is an exploded, perspective view of the valve member of FIG. 1.
Figure 6:
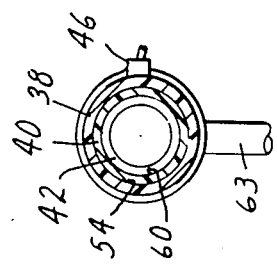
FIG. 6 is a cross-sectional view taken approximately along the line 6—6 of FIG. 4.

The flexible valve member 36 is shown in FIGS. 3, 4 and 6 to preferably comprise an outer tube 38, an inner, flexible tube 40, two support bands 42 and 44, and two circumferential clamps 46 and 48. The outer tube 38 is preferably comprised of a rigid plastic such as 85-100 durometer polyvinyl chloride and has an inlet opening 50 which preferably coincides with the inlet opening 28 described earlier, an outlet opening 52 and a through passageway 54 between openings 50 and 52. The inner, flexible tube 40 is preferably comprised of an elastomer such as a medical grade latex and is disposed within the passageway 54 of the outer tube 38. The inner tube 40 has an inlet opening 56 which preferably coincides with the inlet openings 28 and 50 described earlier, an outlet opening 58 and a through passageway 60 between the openings 56 and 58. The two support bands 42 and 44 are spaced apart within the passageway 60 of the inner tube 40. The two clamps 46 and 48 are positioned on the outside of the outer tube 38 with the clamp 46 opposite the band 42 and the clamp 48 opposite the band 44. The clamps 46 and 48 are tightened sufficiently to circumferentially seal the outer tube 38 to the inner tube 40 between the clamp 46 and the band 42 and between the clamp 48 and the band 44 so that the passageways 34, 54 and 60 coincide between the bands 42 and 44; i.e., the passageway 54 of the outer tube 38 is through the passageway 60 of the inner tube 40 between the bands 42 and 44.

Figure 5:
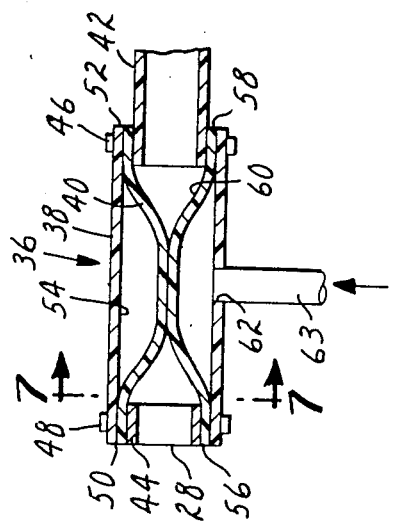
FIG. 5 is a longitudinal, cross-sectional view of the valve member of FIG. 1 in the closed position.

As shown in FIG. 4, a portion of the outer tube 38 has an aperture 62 therethrough located between the support bands 42 and 44. A fluid can be passed through this aperture 62, via a hollow tube connector 63, to distend the inner flexible tube 40, as shown in FIGS. 4 and 5, and thereby control the size of the passageway 60 through the inner tube 40 and, hence, the size of the passageway 34, in a manner to be explained.

As further shown in FIG. 2, the band 42 is preferably an integral portion of a hollow connector 64. The connector 64 comprises a portion of the passageway 34 of the medical catheter 10, the inlet opening 30 described earlier, an outlet opening 66 and, preferably, a third inlet opening 68 of the infusion catheter 10. Fluids can be passed through the second and third inlet openings 30 and 68 and into the passageway 34 via hollow tube connectors 70 and 72, respectively. Tube connectors 70 and 72 are shown to be integral portions of the connector 64. The tube connector 70 preferably defines an angle of about 45 to 90 degrees, and most preferably 45 degrees, with the general direction of the passageway 34 and the tube connector 72 preferably defines an angle of about 90 degrees, for reasons to be explained.

The outlet opening 66 of the connector 64 is covered by a length of suitable medical grade tubing 74 such as 68 durometer polyvinyl chloride tubing available from Natvar Company, a division of High Voltage Engineering, Clayton, N.C. The end portion of the tubing 74 overlapping the connector 64 is preferably circumferentially sealed thereto by, for example, a suitable clamp 76. The end portion of the tubing 74 immediately adjacent the outlet opening 32 is preferably angled back with respect to a plane to form a wedge-like shape to ease insertion into the aorta as will be explained.

As shown in FIG. 1, there are three connections between the medical catheter 10 and the remainder of the system 12. One connection is between the tube connector 70 and a conventional temperature sensor and gauge 78 via a tubing 80. A suitable temperature sensor and gauge 78 is available from Sarns Inc. Ann Arbor, MI. The temperature sensor and gauge 78, in turn, is connected to an outlet from the heat exchanger 24 via a tubing 82. A suitable heat exchanger 24 and heater 26 is available from Sarns Inc. Ann Arbor, Mich. An inlet to the heat exchanger 24 is connected to an outlet from the blood pump 22 by a tubing 84. A suitable blood pump 22 is available from Sarns Inc. Ann Arbor, Mich. An inlet to the blood pump 22 is connected to an outlet from the blood reservoir 20 via a tubing 86. A suitable blood reservoir 20 is available from Sarns Inc. Ann Arbor, Mich. An inlet to the blood reservoir 20 is connected to an outlet from the blood separator 18 via tubing 88. A suitable blood separator 18 is available from Haemonetics Corporation, Braintree, Massachusetts. Suitable tubing for tubings 80, 82, 84, 86 and 88 is available from Norton Industrial Plastics, Akron, Ohio. All of the connections are preferably conventional and well known in the art.

A second connection between the infusion catheter 10 and the remainder of the system 12 is between the tube connector 72 and a pressure monitor 90 via a tubing 92. A suitable monitor 90 is available from Data Instruments Inc., Lexington, Mass. As with the other connections, this connection and the tubing 92 is preferably conventional and well known in the art.

Figure 7:
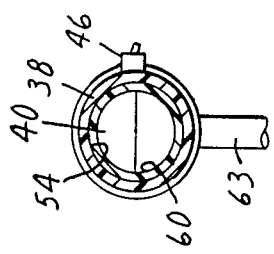
FIG. 7 is a cross-sectional view taken approximately along the line 7—7 of FIG. 5.

A third connection is between the connector 63 and a source of fluid pressure to distend the inner, flexible tube 40 as shown in FIGS. 5 and 7. The source of fluid pressure is shown in FIG. 1 to be a conventional syringe pump 94. The syringe pump 94 is shown connected to the connector 63 by a conventional tubing 96. Again, the actual connections are conventional and well known in the art.

The manner by which the tubing 40 can be distended by fluid pressure from the syringe pump 94 will next be described. As shown in FIG. 1, the syringe pump 94 is provided with a conventional valve member 98. The valve member 98 allows air to be drawn into a pump chamber 100 within the syringe pump 94 via an inlet opening 102. The inlet opening 102 is in communication with the chamber 100 when the valve member 98 is in a first position. The air is drawn into the chamber 100 by a vacuum that can be created by a piston 104 in conventional fashion when the valve member 98 is in the first position.

Once the air has been drawn into the chamber 100, the valve member 98 can be moved to a second position blocking off the path between the chamber 100 and the outside and opening up a path between the chamber 100 and the tubing 96. This allows air to be forced by the piston 104 through valve member 98 and through the tubing 96 and into the area between the tubings 38 and 40 of the valve member 36. This, in turn, distends the tubing 40 as shown in FIGS. 5 and 7 to control the size of the passageway 60 and, hence, the passageway 34. As shown in cross-sectional view in FIG. 7, this can result in the total closure of the passageway 34, or this can result in the closure of the passageway 34 around an occlusion catheter 106 in a manner to be explained.

The conventional occlusion catheter 106 is shown in FIGS. 1 and 8 to be comprised of an inlet opening 108, and expandable occluder 110 and a through passageway 112 between the inlet opening 108 and the expandable occluder 110. A syringe pump 114, similar to the syringe pump 94, is shown connected to the inlet opening 108 to forcibly expand the occluder 110 with a fluid, preferably a sterile acqueous saline solution, in conventional fashion. A suitable occlusion catheter 106 is a Fogarty occlusion catheter available from American Hospital Supply Corp., McGaw Park, Ill.

The method by which the medical catheter 10 and the occlusion catheter 106 can be used to rapidly infuse a patient with blood will next be described generally in relation to FIGS. 1 and 8. Referring specifically to FIG. 8, the patient 16 is shown in schematic view with portions broken away to expose a ruptured aortic aneurysm 116. The aneurysm 116 is located in an aorta 118 at a place downstream in the normal flow of blood from a heart and a brain, not shown, lungs 120, a liver 122 and kidneys 124. The medical catheter 10 and the occlusion catheter 106 are shown inserted into the aorta 118 with the occlusion catheter extending beyond the medical catheter 10 with the expandable occluder 110 positioned at a place within the aorta 118 located upstream of the aneurysm 116 and downstream of the kidneys 124, in the normal flow of blood from the heart.

The medical catheter 10 is inserted into the aorta 118 using conventional and well known techniques. Typically, this would involve making a stab wound in the ascending aorta proximal to the innominate artery and inserting the medical catheter 10 so that the outlet 32 of the medical catheter 10 is directed towards the descending aorta. Initially during this insertion step, the flexible valve member 36 is preferably open as shown in FIGS. 4 and 6 to allow any entrapped air to be purged from the system 12. After this air is purged, the valve member 36 is preferably closed as shown in FIGS. 5 and 7 to minimize blood loss. Care should be taken not to open the portion of the chest overlying the diaphragm 126 and generally towards the aneurysm 116. This could result in the instant decompression and loss of blood pressure referred to earlier.

By inserting the medical catheter 10 into the aorta 118 from a site through the chest that generally overlies the aorta upstream of the diaphragm, whatever blood pressure that remains should be preserved. By way of further explanation, the diaphragm 126 can act as a natural barrier to internal bleeding after the aneurysm 116 ruptures. The diaphragm 126 restrains the blood from flowing throughout the thoracic cavity. Instead, the blood is generally kept in the area of the aneurysm 116 by the diaphragm 126, and a reduced blood pressure still exists. If this area was accessed by, for example, first cutting open the abdomen in the area of the ruptured aneurysm 116, even this reduced blood pressure could be lost.

Once the medical catheter 10 is inserted into the aorta 118, the medical catheter 10 is extended sufficiently into the aorta 118 to insure that the outlet 32 is downstream of the ostiae at the apex of the aortic arch. Next, with the inlet opening 28 disconnected from the passageway 34 through the connector 64 by the distention of the flexible tube 40, i.e., with the valve member 36 closed as shown in FIGS. 5 and 7, the blood 14 can be rapidly infused through the medical catheter 10 and into the aorta 118. The blood 14 can, of course, escape through the ruptured aneurysm 116, but the blood 14 will still be generally contained by the diaphragm 126, and the blood pressure can be increased to a more normal level.

The blood 14 that is infused through the medical catheter 10 is pumped from the reservoir 20 by the blood pump 22 in conventional fashion. Before infusion, the blood 14 is suitably warmed by the heat exchanger 24. The temperature and the pressure of the blood 14 can be monitored by the temperature sensor and gauge 78 and the pressure monitor 90, respectively, and this information can be used by the attendant medical personnel to adjust the pump 22 and the heater 26 in conventional fashion.

While the blood pressure is being at least somewhat restored, the occlusion catheter 106 can be received within the medical catheter 10 by inserting the occlusion catheter 106 through the inlet opening 28 of the medical catheter 10 and extending the occlusion catheter 106 downstream into the aorta 118 until the expandable occluder 110 is located immediately upstream of the aneurysm 116 as described earlier. The location of the aneurysm 116 within the aorta 118 can be determined by conventional X-Ray techniques. Insertion of the occlusion catheter 106 into the medical catheter 10 can be facilitated by coating either or both of these catheters 106 and 10 with a suitable lubricant in conventional fashion. A preferred lubricant is Hydromer coating, available from Hydromer, Inc., Whitehouse, New Jersey.

While the occlusion catheter 106 is being axially inserted into the medical catheter 10 through the inlet opening 28, blood loss through the inlet opening 28 is restrained by the valve member 36. More particularly, the air pressure on the flexible tube 40 can be manually reduced sufficiently to allow passage of the occlusion catheter 106 through the valve member 36 but no so greatly to allow a significant loss of blood; the inner flexible tube 40 closes around the occlusion catheter to restrain the passage of the blood through the inlet opening 28 while permitting the passage of the occlusion catheter 106 axially through the valve member 36. In actual practice, it is possible that the valve member 36 may actually be opened momentarily, resulting in some additional blood loss. This can be minimized by quickly inserting the occluder 110 into the inlet opening 28 and closing the valve member 36 around the occlusion catheter 106 as already described.

Once the blood pressure is somewhat restored and the expandable occluder 110 is positioned as described, the occluder 110 can be expanded by the syringe pump 114 as previously described. This expansion effectively isolates the portion of the cardiovascular system lying upstream of the ruptured aneurysm 116 from the portion lying downstream of the aneurysm 116 by restraining the flow of blood past the occluder 110. Once this is accomplished, two further results can be obtained. For one, the portion of the abdomen overlying the ruptured aneurysm 116 can be opened with decreased risk of loss of blood pressure to the critical organs identified earlier. For another, the blood pressure to these critical organs can be further increased to a more normal level by the additional infusion of blood from the reservoir 20 as previously described.

As part of the opening of the abdomen over the ruptured aneurysm 116, a conventional suction catheter 127 can be introduced into the area of the aneurysm 116 and used to remove the internal bleeding. The suction is provided by the blood separator 18 described earlier. The blood 14 removed from the abdomen is returned to the blood separator 18 via a conventional medical tubing 128. The blood separator 18 separates the blood plasma from the remainder of blood and pumps the remainder of the blood to the blood reservoir 20 through the tubing 88. Additional bank blood 130 is introduced into the reservoir 20 to provide the volume necessary to perform the rapid infusion described earlier. As previously explained, the blood 14 pumped from the reservoir 20 through the medical catheter 10 is warmed in conventional fashion by the heat exchanger 24 and the heater 26 and the temperature of the blood 14 can be monitored by the temperature sensor and gauge 78 while the pressure can be monitored by the pressure monitor 90.

The blood 14 enters the medical catheter 10 through the tubing connector 70. As noted earlier, the tubing connector 70 preferably forms an acute angle of approximately 45 degrees with the body of the connector 64. This is believed to provide a smoother transition for the blood 14 from the tubing 80 to the infusion catheter 10 and thereby lessen the potential damage to the blood 14.

Once the blood pressure has been raised to the desired level, the ruptured aneurysm 116 can be repaired or replaced as required in the opinion of the attending medical personnel. After this, the procedure can be completed by deflating the occluder 110, withdrawing the catheters 10 and 106 for the patient and closing the wounds in the aorta 118, the chest and the abdomen in conventional fashion. Withdrawal of the catheters 10 and 106 can be facilitated by first withdrawing the occluder 110 sufficiently to place it within the passageway 34 of the medical catheter 10. Prior to withdrawal of the catheters 10 and 106, it may be desirable to infuse additional blood through the medical catheter 10, as previously described, to replace any additional blood lost during the repair or replacement of the aneurysm 116 and to return the blood pressure to a more normal level before closing the wounds.

From the foregoing, it will be apparent that all of the objectives of this invention have been achieved by the medical catheter and method shown and described. It will also be apparent that various modifications and changes may be made by those skilled in the art without departing from the spirit of the invention as expressed in the accompanying claims. Because these modifications and changes may be made by one skilled in the art and without departing from the spirit of the invention, all matters shown and described are to be interpreted as illustrative and not in a limiting sense.

What is claimed is:

1. A medical catheter suitable for use with an occlusion catheter for infusing fluid into a patient, said occlusion catheter having an inlet opening, an expandable occluder and a passageway therebetween, said medical catheter comprising:
   A. a first inlet opening;
   B. a second inlet opening spaced a distance from said first inlet opening;
   C. an outlet opening;
   D. a passageway connecting said openings, said first inlet opening, said outlet opening and said passageway being dimensioned to receive said occlusion catheter; and
   E. valve means between said first and second inlet openings for controlling the size of a portion of said passageway therebetween to close said passageway and close said passageway around said occlusion catheter, when said occlusion catheter is received within said portion of said passageway, to restrain the passage of fluid through said first inlet opening, said valve means comprising:
      1. an outer rigid tube having an inlet opening, an outlet opening and a passageway between said openings;
      2. an inner flexible tube disposed within said passageway of said outer tube and having an inlet opening, an outlet opening and a passageway between said openings;
      3. two support bands spaced apart within said passageway of said inner tube;
      4. means for sealing said outer tube to said inner, flexible tube opposite said support bands whereby said passageway of said outer tube is through said passageway of said inner tube between said support bands; and
      5. a portion of said outer tube having an aperture therethrough between said support bands so that a fluid can be passed through said aperture to distend said inner, flexible tube and thereby control the size of said passageway through said inner tube between said support bands.

2. The medical catheter according to claim 1 further having a third inlet opening between said second inlet opening and said outlet opening.

3. A method of infusing blood into a patient to increase the blood pressure of the patient upstream of an aortic rupture, said method comprising the steps of:
   A. providing a medical catheter suitable for use with an occlusion catheter for infusing fluid into a patient, said occlusion catheter having an inlet opening, an expandable occluder and a passageway therebetween, said medical catheter comprising:
      1. a first inlet opening;
      2. a second inlet opening spaced a distance from said first inlet opening;
      3. an outlet opening;
      4. a passageway connecting said openings, said first inlet opening, said outlet opening and said passageway being dimensioned to receive said occlusion catheter; and
      5. valve means between said first and second inlet openings for controlling the size of a portion of said passageway therebetween to close said passageway and close said passageway around said occlusion catheter, when said occlusion catheter is received within said portion of said passageway, to restrain the passage of fluid through said first inlet opening;
   B. inserting said medical catheter directly into said patient's aorta;
   C. infusing blood directly into said aorta through said second inlet opening of said medical catheter to raise said blood pressure before opening said patient's abdomen;
   D. inserting said occlusion catheter into said medical catheter through said first inlet opening of said medical catheter;
   E. extending said expandable occluder of said occlusion catheter into said aorta upstream of said aortic rupture; and
   F. expanding said occluder to restrain the flow of said blood within said aorta past said occluder, whereby a portion of the cardiovascular system upstream of said aortic rupture is isolated from a portion of the cardiovascular system downstream of said aortic rupture, so that said patient's abdomen can be opened with decreased risk of loss of said blood pressure.

4. The method according to claim 3 further comprising the step of infusing additional blood through said second inlet opening of said medical catheter to further raise said blood pressure upstream of said aortic rupture.

* * * * *